(12) United States Patent
Cohen

(10) Patent No.: US 7,018,805 B2
(45) Date of Patent: Mar. 28, 2006

(54) α-AMYLASE ASSAY AND USES THEREOF

(75) Inventor: Barb A. Cohen, Watertown, MA (US)

(73) Assignee: Vicam L.P., Watertown, MA (US)

( * ) Notice: Subject to any disclaimer, the term of this patent is extended or adjusted under 35 U.S.C. 154(b) by 279 days.

(21) Appl. No.: 10/230,969

(22) Filed: Aug. 29, 2002

(65) Prior Publication Data

US 2004/0043116 A1    Mar. 4, 2004

(51) Int. Cl.
G01N 33/573 (2006.01)
G01N 33/53 (2006.01)
G01N 33/544 (2006.01)
G01N 33/539 (2006.01)
C12Q 1/40 (2006.01)

(52) U.S. Cl. .................. 435/7.4; 435/22; 435/7.1; 435/96; 435/201; 436/528; 436/539

(58) Field of Classification Search .............. 435/7.1, 435/7.4, 22, 201, 96; 436/528, 539
See application file for complete search history.

(56) References Cited

U.S. PATENT DOCUMENTS

| | | | |
|---|---|---|---|
| 4,622,295 A * | 11/1986 | Ikenaka et al. ............. | 435/22 |
| 5,491,068 A | 2/1996 | Benjamin et al. | |
| 5,840,504 A | 11/1998 | Blecher | |
| 6,362,008 B1 | 3/2002 | Kohn et al. | |

FOREIGN PATENT DOCUMENTS

| WO | WO 97/21831 A1 | 6/1997 |
|---|---|---|
| WO | WO 98/54973 A1 | 12/1998 |
| WO | WO 00/28319 A1 | 5/2000 |
| WO | WO 04/020970 | 3/2004 |

OTHER PUBLICATIONS

Belderok B, Developments in bread-making processes. *Plant Foods Hum Nutr*, (2000) 55(1):1-86.
Collado, et al. "Accurate estimation of sweetpotato amylase activity by flour viscosity analysis." *J. Agric. Food Chem.* (1990) 47:832-835.
CRC For Quality Wheat Products and Processes, "Exploring CRC Research Argricultural Highlights: CRC for Quality Wheat Products and Processes: Gene research finds niche market." No Date.
Crosbie, G.B., et al. "The application of the flour swelling volume test for potential noodle quality to wheat breeding lines affected by sprouting." *J. Cereal Science* (1993) 18: 267-276.
Cuatrecasas, P. and Anfinsen, C., *Meth. Enzymol.* (1971) 22:351-378.
Fox, J.D, and Robyt, J.F. Miniaturization of three carbohydrate analyses using a microsample plate reader. *Anal Biochem* (1991) May 15;195(1):93-6.
Linko, Y-Y, et al. Starch conversion by soluble and immobilized alpha-amylase. *Biotechnology and Bioengineering*, (1975) 18:153-165.
Manelius, R., et al. "The effect of Ca 2+ ions on the alpha-amylolysis of granular starches from oats and waxy-maize." *J. Cereal Science* (1996), 24:139-150.
Megazyme International Ireland Ltd., "Megazyme, Amylazyme Alpha-Amylase Assay Procedure: for the measurement of cereal and microbial alpha-amylases." Dated Jul. 1998.
Molecular Probes Inc. "Detecting Glycosidases." Handbook of Fluorescent Probes and Research Chemicals, (1996). Section 10.2, pp. 1-14.
Molecular Probes, Inc. EnzChek ™ amylase assay kit (E-11954) Product Information. MP-11954. (1999) Revised: Oct. 23, 2001.
No Authors Listed, "Measuring enzyme activity." *Lallemand Baking Update* (1996) 1(15):1-et seq.
No Authors Listed, "Standardizing enzyme levels in flour." *Lallemand Baking Update* (1996) 1(15):1-et seq.
Rani, K.U. et al. "Distribution of enzymes in wheat flour mill streams." *J. Cereal Science* (2001) 34:233-242.
Rinderknecht H, Wilding P, Haverback BJ., A new method for the determination of alpha-amylase. *Experientia* (1967) Oct. 15;23(10):805.
Wong, D.W.S., et al. "Microassay for rapid screening of alpha-amylase activity." *J. Agric. Food Chem.* (2000) 48: 4540-4543.

(Continued)

Primary Examiner—Maryam Monshipouri
Assistant Examiner—Rosanne Kosson
(74) Attorney, Agent, or Firm—Wolf, Greenfield & Sacks, P.C.

(57) ABSTRACT

This invention relates to methods and kits for measuring α-amylase activity in grain and plant products such as flour or stock.

25 Claims, No Drawings

OTHER PUBLICATIONS

Yang, S-S, et al. "Protease and amylase production of *Streptomyces rimosus* in submerged and solid state cultivations." *Bot, Bull. Acad. Sin.* (1999) 40:259-265.

Sandstedt, R. M. et al., A Standardized Wohlgemuth Procedure for Alpha-Amylase Activity. Department of Agricultural Chemistry, University of Nebraska, Annual Meeting, pp. 712-723, May 1939.

Institute of Medicine Food Chemicals Codex, 4$^{th}$ Edition, pp. 1451-1454, 2000.

* cited by examiner

α-AMYLASE ASSAY AND USES THEREOF

FIELD OF THE INVENTION

This invention relates to methods and kits for measuring α-amylase activity in grain products such as flour.

BACKGROUND OF THE INVENTION

The use of flour produced through the processing of cereal grains such as wheat, rye, and oats is an important feature in nutrition and food production around the world. Grains are grown, harvested, and milled into flours, which are used to make breads, bakery products, pastas, all of which are staples in the diet of many individuals world wide. Grains and grain products are also utilized for brewing and fermentation.

Wheat flour is an important ingredient in home baking and is the foundation for almost every commercially baked product and pasta. Of the grains available for the production of flour, wheat is unique in that it is the only cereal grain with sufficient gluten content to make a loaf of bread without being mixed with another grain. Wheat is grown all over the world and is the most widely distributed cereal grain. In general, a reference to "flour" is a reference to wheat flour. Flour is used extensively in the food industry and a key requirement in that industry is the uniform high quality and performance of flour and grains in food and beverage production (For review see: *Plant Foods for Human Nutrition*, Vol 55:1–86, 2000).

Cereal grains store energy as starch, and to perform well in baking and food production, it is important to optimize the level of starch in flour. A key factor in the breakdown of starch in flours is the presence of α-amylase activity in cereal grain flours. α-amylase is an endoenzyme that is present in cereal grains and breaks the α-1,4, glucosidic bonds that are present in starch. The enzyme works in an almost random manner and the effect of its enzymatic activity is the breakdown in the size of the starch molecules and the conversion of starch to sugar.

To help ensure efficient food production methods, it is important to be able to accurately assess the level of α-amylase activity in batches of flour. The presence of excess α-amylase activity flour results in a reduction in the value of the flour for baking. For example, excess starch breakdown in flour can result in sticky or doughy bread that can't be cut in automated loaf-slicing machinery and is therefore unsuitable for commercial production. Insufficient α-amylase activity in flour can also reduce the value of a flour for baking and food production. Insufficient α-amylase activity in flour can result flour that lacks the necessary levels of sugars for proper fermentation and yeast activity in baking. Because of the financial importance of flour quality in the baking and food production industries, it is important to have reliable, reproducible, and easy-to-use methods to determine the amount of α-amylase activity in flours.

Current methods to determine the level of α-amylase in flour include techniques such as the Hagberg-Perten Falling Number test. This is a viscosity-based method in which a flour suspension is heated to gelatinize the starch. The viscosity of the mixture is determined by putting the suspension into a long narrow tube of defined dimensions and measuring the rate at which various calibrated small stirrers or a rod falls though the suspension in the tube. Although the Falling Number test is currently accepted as the industry standard, it does not measure the actual α-amylase enzyme activity level directly, and it is the activity of the enzyme that affects baked good texture and value.

Alternative methods that directly measure α-amylase enzyme activity have been developed, but are not used to directly test flour or stock samples, which limits their usefulness. The availability of a method to directly determine α-amylase enzyme activity in flour or stock samples would provide a more accurate prediction of a flour's or stock's performance, and therefore its value in the baking industry and in other food and beverage production industries.

SUMMARY OF THE INVENTION

The invention is based, in part, on our surprising discovery that the level of α-amylase enzyme activity in a flour sample can be determined by contacting a sample from a grain flour or other grain or plant product with a detectably labeled starch substrate and determining the amount of hydrolysis of the substrate as a measure of the activity of the of α-amylase enzyme activity in the sample.

According to one aspect of the invention, methods for measuring α-amylase activity in a flour or stock sample are provided. The methods include forming a reaction mixture by contacting a sample with a detectably labeled starch substrate for a time sufficient for α-amylase in the sample to hydrolyze the starch substrate, thereby releasing soluble detectably labeled starch fragments, separating the soluble detectably labeled starch fragments from the reaction mixture, and determining the level of hydrolysis of the detectably labeled starch substrate as a measurement of α-amylase activity in the flour or stock sample. In some embodiments, the sample is a flour sample. In certain embodiments, the sample is a stock sample.

In some embodiments, determining the level of hydrolysis of the detectably labeled starch substrate includes quantifying the detectably labeled starch substrate. In other embodiments, determining the level of hydrolysis of the detectably labeled starch substrate includes quantifying the soluble detectably labeled starch substrate fragments. In some embodiments, the method also includes calculating the α-amylase activity in the sample by correlating the quantity of detectably labeled starch to an α-amylase standard. In some embodiments, the method also includes calculating the α-amylase activity in the sample by correlating the quantity of soluble detectably labeled starch fragments to an α-amylase standard. In certain embodiments, the detectably labeled starch substrate is a waxy maize starch. In certain embodiments, the detectably labeled starch substrate includes D-glucose residues and is labeled on about one of every 5–20 D-glucose residues of the starch substrate. In some preferred embodiments, the detectably labeled starch substrate is labeled on about one of every 10–15 D-glucose residues of the starch substrate. In some embodiments, the starch substrate is detectably labeled with a label compound selected from the group consisting of fluorescent, enzyme, radioactive, metallic, biotin, chemiluminescent, bioluminescent, and chromophore molecules. In some embodiments, the label is a fluorophore. In certain embodiments, the fluorophore is selected from the group consisting of fluorescein isothiocyanate (FITC) and Marina Blue.

In some embodiments, the step of separating the soluble detectably labeled starch fragments from the reaction mixture includes filtering the reaction mixture to remove from the mixture detectably labeled starch substrate. In some embodiments, the step of filtering includes the addition of a filtration aid selected from the group consisting of resin, glass beads, beads, and celite. In some embodiments, the step of separating the soluble detectably labeled starch fragments from the reaction mixture includes centrifuging the reaction mixture to remove from the mixture detectably labeled starch substrate. In some embodiments, the method also includes measuring an aliquot of the supernatant of the centrifuged reaction mixture. In certain embodiments, the step of separating the soluble detectably labeled starch fragments from the reaction mixture includes obtaining an aliquot of the reaction mixture and centrifuging the aliquot of the reaction mixture to remove from the aliquot detectably labeled starch substrate. In some embodiments, the step of separating the soluble detectably labeled starch fragments from the reaction mixture includes contacting the fragments with an agent that binds to the detectably labeled starch fragments. In certain embodiments, the agent is a lectin. In other embodiments, the agent is an antibody.

In some embodiments, the sample is an aqueous slurry. In some embodiments, the sample is contacted with the detectably labeled starch substrate for a reaction time of at least about 1 sec, 5 sec, 10 sec, 15 sec, 20 sec, 25 sec, 30 sec, 35 sec, 40 sec, 45 sec, 50 sec, 55 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min. Preferably, the sample is contacted with the detectably labeled starch substrate for a reaction time at least about 1 minute, at least about 5 minutes, at least about 10 minutes, or at least about 15 minutes.

According to another aspect of the invention, methods for measuring α-amylase activity in a flour or stock sample are provided. The methods include forming a reaction mixture by contacting a flour or stock sample with a detectably labeled starch substrate attached to a surface, for a time sufficient for α-amylase in the flour sample to hydrolyze the starch substrate, thereby releasing soluble detectably labeled starch fragments, separating the soluble detectably labeled starch fragments from the reaction mixture, and determining the level of hydrolysis of the detectably labeled starch substrate as a measurement of α-amylase activity in the flour or stock sample. In some embodiments, the sample is a flour sample. In other embodiments, the sample is a stock sample.

In some embodiments, the surface is selected from the group consisting of a tube, a centrifuge tube, a cuvette, a dipstick, a multiwell plate, a slide, a coverslip, a card, a bead, and a plate. In some embodiments, determining the level of hydrolysis of the detectably labeled starch substrate includes quantifying the soluble detectably labeled starch substrate fragments. In some embodiments, the method also includes calculating the α-amylase activity in the sample by correlating the quantity of soluble detectably labeled starch fragments to an α-amylase standard.

In some embodiments, determining the level of hydrolysis of the detectably labeled starch substrate includes quantifying the detectably labeled starch substrate after separating the soluble detectably labeled starch fragments from the reaction mixture. In some embodiments, the method also includes releasing the detectably labeled starch substrate from the surface after separating the soluble detectably labeled starch fragments from the reaction mixture. In certain embodiments, determining the level of hydrolysis of the detectably labeled starch substrate includes quantifying the detectably labeled starch substrate after releasing the detectably labeled starch substrate from the surface. In some embodiments, the method also includes calculating the α-amylase activity in the sample by correlating the quantity of detectably labeled starch to an α-amylase standard. In some embodiments, the detectably labeled starch substrate is a waxy maize starch.

In some embodiments, the detectably labeled starch substrate includes D-glucose residues and is labeled on about one of every 5–20 D-glucose residues of the starch substrate. In certain preferred embodiments, the detectably labeled starch substrate is labeled on about one of every 10–15 D-glucose residues of the starch substrate. In some embodiments, the starch substrate is detectably labeled with a label compound selected from the group consisting of fluorescent, enzyme, radioactive, metallic, biotin, chemiluminescent, bioluminescent, and chromophore molecules. In some embodiments, the label is a fluorophore. In some embodiments, the fluorophore is selected from the group consisting of FITC and Marina Blue.

In some embodiments, the step of separating the soluble detectably labeled starch fragments from the reaction mixture includes filtering the reaction mixture to remove from the mixture detectably labeled starch substrate. In certain embodiments, the step of filtering includes the addition of a filtration aid selected from the group consisting of resin, glass beads, beads, and celite. In some embodiments, the step of separating the soluble detectably labeled starch fragments from the reaction mixture includes centrifuging the reaction mixture to remove from the mixture detectably labeled starch substrate. In some embodiments, the method also includes measuring an aliquot of the supernatant of the centrifuged reaction mixture. In some embodiments, the step of separating the soluble detectably labeled starch fragments from the reaction mixture includes obtaining an aliquot of the reaction mixture and centrifuging the aliquot of the reaction mixture to remove from the aliquot detectably labeled starch substrate. In certain embodiments, the step of separating the soluble detectably labeled starch fragments from the reaction mixture includes contacting the fragments with an agent that binds to the detectably labeled starch fragments. In some embodiments, the agent is a lectin. In some embodiments, the agent is an antibody.

In some embodiments, the sample is an aqueous slurry. In some embodiments, the sample is contacted with the detectably labeled starch substrate for a reaction time of at least about 1 sec, 5 sec, 10 sec, 15 sec, 20 sec, 25 sec, 30 sec, 35 sec, 40 sec, 45 sec, 50 sec, 55 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min. Preferably, the sample is contacted with the detectably labeled starch substrate for a reaction time is at least about 1 minute, at least about 5 minutes, at least about 10 minutes, or at least about 15 minutes.

According to yet another aspect of the invention, kits for measuring α-amylase activity in flour or stock are provided. The kits include a first container containing a detectably labeled starch substrate, a second container containing an α-amylase standard, instructions for measuring the α-amylase activity in a flour or stock sample.

According to yet another aspect of the invention, kits for measuring α-amylase activity in flour or stock are provided. The kits include a first container containing a starch substrate, a second container containing an α-amylase standard, a third container containing a detectable label, instructions for labeling the starch substrate, and instructions for measuring the α-amylase activity in a flour or stock sample.

In some embodiments of the foregoing kits, the sample is a flour sample. In other embodiments of the foregoing kits, the sample is a stock sample. In some embodiments of the foregoing kits, the starch substrate is waxy maize starch. In certain embodiments of the foregoing kits, the detectably labeled starch substrate is a waxy maize starch. In some embodiments of the foregoing kits, the detectably labeled starch substrate includes D-glucose residues and is labeled on about one of every 5–20 D-glucose residues of the starch substrate. In some preferred embodiments of the foregoing kits, the detectably labeled starch substrate is labeled on about one of every 10–15 D-glucose residues of the starch substrate. In some embodiments of the foregoing kits, the detectable label is a label compound selected from the group consisting of fluorescent, enzyme, radioactive, metallic, biotin, chemiluminescent, bioluminescent, and chromophore molecules. In certain embodiments of the foregoing kits, the starch substrate is detectably labeled with a label compound selected from the group consisting of fluorescent, enzyme, radioactive, metallic, biotin, chemiluminescent, bioluminescent, and chromophore molecules. In some embodiments of the foregoing kits, the label is a fluorophore. In certain embodiments of the foregoing kits, the fluorophore is selected from the group consisting of FITC and Marina Blue. In some embodiments of the foregoing kits, the instructions for measuring the α-amylase activity in a sample recite a method comprising forming a reaction mixture by contacting a sample with a detectably labeled starch substrate for a time sufficient for α-amylase in the sample to hydrolyze the starch substrate, thereby releasing soluble detectably labeled starch fragments, separating the soluble detectably labeled starch fragments from the reaction mixture, and quantifying the soluble detectably labeled starch as a measurement of α-amylase activity in the sample. In some embodiments of the foregoing kits, the instructions further recite calculating the α-amylase activity in the sample by correlating the quantity of soluble detectably labeled starch fragments to an α-amylase standard.

In some embodiments of the foregoing kits, the step of separating the soluble detectably labeled starch fragments from the reaction mixture includes filtering the reaction mixture to remove from the mixture detectably labeled starch substrate. In some embodiments of the foregoing kits, the step of filtering includes the addition of a filtration aid selected from the group consisting of resin, glass beads, beads, and celite. In some embodiments of the foregoing kits, the step of separating the soluble detectably labeled starch fragments from the reaction mixture includes centrifuging the reaction mixture to remove from the mixture detectably labeled starch substrate. In some embodiments of the foregoing kits, the step also includes measuring an aliquot of the supernatant of the centrifuged reaction mixture. In certain embodiments of the foregoing kits, the step of separating the soluble detectably labeled starch fragments from the reaction mixture includes obtaining an aliquot of the reaction mixture and centrifuging the aliquot of the reaction mixture to remove from the aliquot detectably labeled starch substrate. In some embodiments of the foregoing kits, the step of separating the soluble detectably labeled starch fragments from the reaction mixture includes contacting the fragments with an agent that binds to the detectably labeled starch fragments. In some embodiments of the foregoing kits, the agent is a lectin. In other embodiments of the foregoing kits, the agent is an antibody.

In some embodiments of the foregoing kits, the instructions further recite that the sample is an aqueous slurry. In some embodiments of the foregoing kits, the instructions further recite that the sample is contacted with the detectably labeled starch substrate for a reaction time of at least about 1 sec, 5 sec, 10 sec, 15 sec, 20 sec, 25 sec, 30 sec, 35 sec, 40 sec, 45 sec, 50 sec, 55 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min. Preferably, in some embodiments of the foregoing kits, the instructions recite that the sample is contacted with the detectably labeled starch substrate for a reaction time at least about 1 minute, at least about 5 minutes, at least about 10 minutes, or at least about 15 minutes.

DETAILED DESCRIPTION OF THE INVENTION

For the commercial and home use of flour for baking and food production, it is important to maintain an appropriate level of α-amylase activity in the flour. A level of activity that is too high may result in a product that is sticky and/or doughy and unmarketable; but flour with insufficient α-amylase activity may not contain enough sugar for proper yeast function, resulting in dry, crumbly bread. To augment the level of endogenous α-amylase activity in flour, substitute α-amylase may be added to flour in the form of fungal α-amylase or other α-amylase. Therefore, the ability to determine the level of activity of both endogenous (natural) and fungal α-amylase, or other α-amylase, in a flour sample would benefit the food production process and promote more efficient use of flour in food production.

In addition to the use of grains and other plant products in baking, grains such as barley, oats, wheat, as well as plant components such as corn, hops, and rice are used for brewing, both in industry and for home brewing. The components used in brewing may be unmalted or may be malted, which means partially germinated resulting in an increase in the levels of enzymes including α-amylase. For successful brewing, adequate levels of α-amylase enzyme activity are necessary to ensure the appropriate levels of sugars for fermentation.

As used herein, the term "flour" means milled or ground cereal grain. The term "flour" may also mean Sago or tuber products that have been ground or mashed. In some embodiments, flour may also contain components in addition to the milled or mashed cereal or plant matter. An example of an additional component, although not intended to be limiting, is a leavening agent. Cereal grains include: wheat, oat, rye, and barley, In preferred embodiments of the invention, the cereal grain is wheat. Tuber products include tapioca flour, cassava flour, and custard powder. The term "flour" also includes ground corn flour, maize-meal, rice flour, wholemeal flour, self-rising flour, tapioca flour, cassava flour, ground rice, and custard powder.

As used herein, the term "stock" means grains and plant components that are crushed or broken. For example, barley used in beer production is a grain that has been coarsely ground or crushed to yield a consistency appropriate for producing a mash for fermentation. As used herein, the term "stock" includes any of the aforementioned types of plants and grains in crushed or coarsely ground forms. It will be understood that the methods of the invention may be used to determine α-amylase activity levels in flours, and also in stock, which includes the aforementioned types of grains, tubers, and other plant products that have been crushed.

The invention involves in some aspects, methods for measuring α-amylase activity in flour and grain or tuber products and stock. As used herein, the term "α-amylase" means endogenous α-amylase or α-amylase that has been added to the flour or stock. As used herein, the term "α-amylase" means a protein having α-amylase activity, preferably plant-derived α-amylase and/or microbial α-amylase. Plant-derived α-amylase includes, but is not limited to, wheat α-amylase, and microbial α-amylase includes, but is not limited to, bacterial α-amylase and fungal α-amylase. As used herein, the term "α-amylase activity" means the enzymatic action of the α-amylase. The enzymatic action of the α-amylase includes the hydrolysis (breakage) of the α-1,4, glucosidic bonds present in starch, which reduces the size of the starch molecules and converts the starch into sugar.

The invention involves in some aspects, contacting a flour or stock sample with a starch substrate and determining the activity of the α-amylase enzyme of the sample in the breakdown of the starch substrate. In some aspects of the invention, the starch substrate is detectably labeled. This detectable label is attached to the starch substrate utilizing standard chemistry methods and allows quantification of the amount of cleavage of the starch substrate by α-amylase after it is contacted with the sample. Such standard methods may include, but are not limited to, attaching a detectable label to the starch substrate through chemical conjugation. Various conjugation reagents including, but not limited to, cyanogen bromide and pyridinium dichromate, which may be used to activate hydroxyl groups on the starch. The activated starch will react with the amino groups of fluorescent materials to form the fluorescence-labeled substrate starch.

In some embodiments, the activity of the α-amylase is determined by quantifying the amount of detectably labeled starch substrate fragments that have been cleaved from the starch substrate. In other embodiments, the activity of the α-amylase is determined by quantifying the amount of detectably labeled starch substrate that remains intact following contact with the sample.

The invention involves in some aspects separating the soluble detectably labeled starch fragments from the detectably labeled starch in the reaction mixture. Methods that may be used to separate the fragments from the reaction mixture include, but are not limited to: filtration, centrifugation, and affinity binding methods. As used herein, the term "filtering" means passing the sample through one or more filter devices. Such devices include, but are not limited to paper filters, screens, mesh, etc. Filtering may involve passing the material to be filtered though a single filter, or through a multiple filters, which may be of the same type or may be of differing types (e.g., a screen followed by a paper or a mesh followed by a screen and/or paper filter). Filtration is done using standard methods known in the art. One of ordinary skill in the art will recognize there are numerous filtration methods, combinations, and techniques that are useful in the methods and kits of the invention. In the methods and kits of the invention, filtering methods may also include the use of filtration aids including, but not limited to: resins, beads including glass beads, and celite, which is also known as diatomaceous earth and Kieselguhr. Selection and use of such filtration aids in the methods of the invention, will be understood by one of ordinary skill in the art.

The invention relates in part to the use of centrifugation methods to separate detectably labeled fragments from the reaction mixture. Such methods include the centrifugation and may also include the removal of an aliquot of the supernatant of the centrifugation for measurement of the amount of detectably labeled starch substrate fragments. The removal of an aliquot from the centrifuged reaction mixture may be followed by the centrifugation of the aliquot prior to determination of the level of detectably labeled starch substrate in the aliquot.

The invention also relates in part to the use of affinity binding methods to separate detectably labeled fragments from the reaction mixture. An example of an affinity binding method, although not intended to be limiting, is the use of affinity chromatography methods to separate detectably labeled fragments from the reaction mixture. Affinity binding methods include the use of agents that bind to the molecules to be separated. Such agents include, but are not limited to, lectins and antibodies. As will be recognized by one of ordinary skill in the art, the agent may be bound to a support, e.g. as in affinity column chromatography. It will be understood that in alternative embodiments, the agent is not bound to a surface. Methods of separating molecules using methods such as affinity binding and/or affinity chromatography are well understood by those of ordinary skill in the art. Examples of affinity separation methods are provided in U.S. Pat. No. 6,362,008, which is hereby incorporated by reference in its entirety.

One of ordinary skill in the art will recognize that following a separation step as described herein, either the soluble detectably labeled substrate fragments, the detectably labeled substrate, or both, can be measured using the methods of the invention to determine the α-amylase activity in the sample tested. Such measurements may be done using standard methods, including, but not limited to, transferring the supernatant or filtrate samples to a measurement cuvette, followed by measurement on a calibrated fluorometer. In such readings, the fluorescent reading would be proportional to the amount of amylase presented in the flour or stock samples.

As used herein the term "time sufficient for α-amylase to hydrolyze the starch substrate" means the amount of time for hydrolysis to occur. The time sufficient is at least about 1 sec, 5 sec, 10 sec, 15 sec, 20 sec, 25 sec, 30 sec, 35 sec, 40 sec, 45 sec, 50 sec, 55 sec, 1 min, 2 min, 3 min, 4 min, 5 min, 6 min, 7 min, 8 min, 9 min, 10 min, 11 min, 12 min, 13 min, 14 min, 15 min, 16 min, 17 min, 18 min, 19 min, 20 min, 21 min, 22 min, 23 min, 24 min, 25 min, 26 min, 27 min, 28 min, 29 min, 30 min, 31 min, 32 min, 33 min, 34 min, 35 min, 36 min, 37 min, 38 min, 39 min, 40 min, 41 min, 42 min, 43 min, 44 min, 45 min, 46 min, 47 min, 48 min, 49 min, 50 min, 51 min, 52 min, 53 min, 54 min, 55 min, 56 min, 57 min, 58 min, 59 min, or 60 min. Preferably, the time is at least 1 minute, at least 5 minutes, at least 10 minutes, or at least 15 minutes.

As used herein the term: "hydrolysis" means at least partial hydrolysis of the starch substrate. Total hydrolysis of the starch substrate is not required. As used herein, the term "soluble detectably labeled starch fragments" means fragments of the detectably labeled starch that have been released from the starch by hydrolysis. The soluble detectably labeled starch fragments are no longer attached to the starch substrate.

In some embodiments of the invention, a control sample may be prepared. As used herein the term "control sample" means a sample with a known amount of α-amylase activity that may be contacted with a starch substrate identical to that contacted with the flour or stock test sample. The reaction with the known amount of α-amylase activity thereby serves as a control reaction from which one of ordinary skill can extrapolate the level of activity in the test sample. One of ordinary skill in the art will recognize how to prepare and utilize a control reaction to allow determination of the α-amylase activity in test samples.

The invention includes a starch substrate that is detectably labeled. As used herein, a "starch substrate" is a starch molecule upon which α-amylase acts enzymatically. As used herein, the term "starch" includes, but is not limited to, wheat starch, waxy wheat starch, corn starch, waxy maize starch, oat starch, rice starch, tapioca starch, mung-bean starch, potato or high amylose starches, and sorghum starch. In preferred embodiments, the starch substrate is waxy maize starch, which is also known as amylopectin.

As used herein, a starch substrate or starch substrate fragment that is "detectably labeled" means a starch substrate or substrate fragment to which a label that can be detected is attached. The term "label" as used here means a molecule preferably selected from, but not limited to, the group consisting of fluorescent, enzyme, radioactive, metallic, biotin, chemiluminescent, bioluminescent, chromophore, colored, or absorbent molecules. In some aspects of the invention, a label may be a combination of the foregoing molecule types.

Radioactive or isotopic labels include, for example, $^{14}C$, $^{3}H$, $^{35}S$, $^{125}I$, and $^{32}P$. Fluorescent labels include any compound that emits an electromagnetic radiation, preferably visible light, resulting from the absorption of incident radiation and persisting as long as the stimulating radiation is continued. Such compounds include coumarin containing molecules, and further include anthroyl compounds, naphthalene compounds, pyrene compounds, compounds containing benzyl, pyrenyl and phenyl groups, fluorescein compounds, anthracene compounds, compounds containing conjugated pi electron systems, but are not limited to these categories of compounds and include any compound that could be used as a label in this invention.

Examples of the fluorescent coumarin molecules include 7-hydroxycoumarin, 7-aminocoumarin, and further include 6-((7-amino-4-methylcoumarin-3-acetyl)amino)hexanoic acid, succinimidyl ester, 7-amino-3-((((succinimidyl)oxy) carbonyl)methyl)-4-methylcoumarin-6-sulfonic acid, 7-diethylaminocoumarin-3-carboxylic acid, 7-diethylaminocoumarin-3-carboxylic acid succinimidyl ester, 7-diethylamino-3-(4'-isothiocyanophenyl)-4-methylcoumarin, 7-dimethylaminocoumarin-4-acetic acid, 7-dimethylaminocoumarin-4-acetic acid succinimidyl ester, 7-hydroxycoumarin-3-carboxylic acid, 7-hydroxycoumarin-3-carboxylic acid succinimidyl ester, 7-hydroxy-4-methylcoumarin-3-acetic acid, 7-hydroxy-4-methylcoumarin-3-acetic acid succinimidyl ester, 7-methoxycoumarin-3-carboxylic acid, 7-methoxycoumarin-3-carboxylic acid succinimidyl ester, 7-diethylaminocoumarin-3-carbonyl azide and 7-methoxycoumarin-3-carbonyl azide.

Examples of naphthalene compounds include 6-((5-dimethylaminonaphthalene-1-sulfonyl)amino)hexanoic acid, 2-dimethylaminonaphthalene-5-sulfonyl chloride, dimethylaminonaphthalene-6-sulfonyl chloride, 6-(N-methylanilino)naphthalene-2-sulfonyl chloride, 6-(p-toluidinyl) naphthalene-2-sulfonyl chloride and 5-acenaphthalene.

Examples of other fluorescent labels include but not limited to 2,4-dinitrophenyl, acridine, cascade blue, rhodamine, 4-benzoylphenyl, 7-nitrobenz-2-oxa-1,3-diazole, 4,4-difluoro-4-bora-3a,4a-diaza-3-indacene and fluorescamine. Absorbance-based labels include molecules that are detectable by the level of absorption of various electromagnetic radiation. Such molecules include, for example, the fluorescent labels indicated above, as well as various dyes that are visibly colored and examinable by the eye, such as indole derivatives, which are detectable by colorimetric means.

Chemiluminescent labels in this invention refer to compounds that emit light as a result of a non-enzymatic chemical reaction.

As used herein, fluorophores include, but are not limited to amine-reactive fluorophores that cover the entire visible and near-infrared spectrum. Examples of such fluorophores include, but are not limited to, 4-methylumbelliferyl phosphate, fluorescein isothiocyanate (FITC), tetramethylrhodamine isothiocyanate (TRITC), BODIPY dyes; Oregon Green, rhodamine green dyes; the red-fluorescent Rhodamine Red-X, Texas Red dyes; and the UV light-excitable Cascade Blue, Cascade Yellow, Marina Blue, Pacific Blue and AMCA-X fluorophores. Fluorophores may also include non-fluorescent dyes used in fluorescence resonance energy transfer (FRET).

Chromophores that are useful in the invention include, but are not limited to, chromogenic substances such as 4-nitrophenylphosphate, 3,3',5,5'-tetramethylbenzidine and 2,2'azino-di-[3-ethelbenz-thiazoliane sulfonate (6)] In addition to alkaline phosphatase and peroxidase, other enzymes that can be used in methods and kits of the invention include, but are not limited to β-galactosidase, β-glucuronidase, α-glucosidase, β-glucosidase, α-mannosidase, galactose oxidase, glucose oxidase and hexokinase.

The labeled molecules of the invention can be prepared from standard moieties known in the art. As is recognized by one of ordinary skill in the art, the labeling process will vary according to the molecular structure of the detectable label. For fluorescent materials with free amino groups, a typical process, though not intended to be limiting, would be to use alkaline cyanogen bromide to activate starch substrate. The cyanogen-bromide-activated starch attacks the free amino group of the fluorophores to form a new peptide bond, which links the fluorophores onto the starch substrate. Other methods of labeling molecules with one or more of the above-identified types of detectable labels are routinely used and are well understood by those of ordinary skill in the art.

The invention involves, in some embodiments, a labeled starch substrate that is labeled on about one of every 5–20 D-glucose residues of the starch. In other embodiments, the invention involves a labeled starch substrate that is labeled on about one of every 10–15 D-glucose residues of the starch.

The invention in another embodiment, includes measuring α-amylase activity in a flour or stock sample by forming a reaction mixture by contacting the sample with a detectably labeled starch substrate attached to a surface, for a time sufficient for the α-amylase enzyme to hydrolyze the starch substrate. As used herein the term "surface" means a material including any synthetic or natural material. Examples of surfaces of the invention include, but are not limited to: glass, plastic, nylon, metal, paper, cardboard, and can be in numerous forms including, but not limited to, tubes, centrifuge tubes, cuvettes, cards, slides, dipsticks, beads, coverslips, multiwell plates, Petri plates, etc. One of ordinary skill in the art will recognize that numerous additional types of surfaces can be used in the methods of the invention.

As used herein the term "attached to a surface" means chemically or biologically linked to the surface and not freely removable from a surface. Examples of attachment, though not intended to be limiting are covalent binding between the surface and the starch substrate, attachment via specific biological binding, or the like. For example, "attached" in this context includes chemical linkages, chemical/biological linkages, etc. As used herein the term "covalently attached" means attached via one or more covalent bonds. As used herein the term "specifically attached" means a species is chemically or biochemically linked to a surface as described above with respect to the definition of "attached," but excluding all non-specific binding. In the methods of the invention, a starch substrate that is attached to a surface is attached such that the substrate is not removable from the surface without specific stripping methods or solutions. Such stripping methods may include, but are not limited to, physical methods such as scraping or heating, enzymatic methods, and chemical methods, which may include but are not limited to contacting the attached substrate and surface with a solution such that the link between the substrate and the surface is broken and the substrate is released.

One of ordinary skill in the art will be able to envision the steps of forming a reaction mixture by contacting a detectably labeled starch substrate attached to a surface with an α-amylase enzyme and removing the labeled fragments from the reaction mixture. The amount of label present on the fragments released by the hydrolysis (soluble fragments) is measured and/or the amount of label that remains on the starch that has not been hydrolyzed and therefore remains attached to the surface is measured, and either or both measurements are to be compared to the initial amount of label on the surface prior to contact with the α-amylase enzyme. From a comparison of the levels of labeled starch before and after hydrolysis, a determination of the amount of α-amylase activity in the reaction mixture can be made. One of ordinary skill in the art will recognize that the total amount of detectably labeled starch prior to contact with the α-amylase, can be compared with either the level of label on pieces released by α-amylase hydrolysis, or the amount of delectably labeled substrate that remains attached to the surface following hydrolysis. This type of method can be used to determine the amount of α-amylase enzyme activity in the flour or stock sample or control sample.

The following illustrates the use of a method of the invention to determine the level of α-amylase activity in a flour or stock sample. For example, if detectably labeled starch is contacted with a flour or stock sample for a time sufficient to hydrolyze the starch and subsequent measurement of the amount of delectably labeled starch substrate fragments that are not attached to the surface is determined to be zero, it indicates the absence of α-amylase activity in the flour or stock sample tested. In addition, the determination that the original amount of delectably labeled starch substrate that was attached to the surface remains attached to the surface, indicates that there is no α-amylase activity in the sample. In contrast, if the sample contains α-amylase, the enzyme will break down the starch substrate and the hydrolyzed substrate fragments will be released or solubilized. After separation of the hydrolyzed, small-sized starch fragments from the non-hydrolyzed starch substrate, fluorescence from either the starch fragments or the non-hydrolyzed starch substrate can be measured to determine quantity of α-amylase activity in the sample. The amount of α-amylase activity in the flour or stock sample will be positively proportional to the fluorescent reading in the starch fragments, but inversely proportional to the fluorescence in the non-hydrolyzed starch substrate.

In some embodiments of the invention, the reaction mixture includes delectably labeled starch substrate attached to a surface such as a test tube or centrifuge tube, which is contacted with α-amylase in a sample. Following contact for a time sufficient for α-amylase to hydrolyze the starch substrate, the hydrolyzed starch substrate fragments that are not attached to the surface can be separated from the non-hydrolzyed substrate and measured, and/or the delectably labeled starch substrate that remains attached to the surface may be measured as attached to the tube, or may be stripped off the surface and its quantity determined. For example, to strip off the delectably labeled starch substrate attached to the surface, the surface may be treated with physical or chemical methods. The amount of stripped delectably labeled starch substrate is then collected and the level of labeled starch substrate is measured as a determination of the activity level of α-amylase in the sample. One of ordinary skill in the art will recognize that prior to determination the activity level, a purification step such as, but not limited to, centrifugation, filtration, or affinity binding methods, may-be used to further separate the soluble detectably labeled fragments. Following the separation, a determination of the amount of soluble detectably labeled fragments and/or retained substrate is done. This determination may be done using a routine detection method, which can be selected based on the type of detectable label utilized. Examples of such methods, include, but are not limited to the use of a fluorometer to determine the amount of detectably labeled fragments or retained substrate when the label is fluorescence, or the use of a scintillation counter if the label is radioactive. One of ordinary skill in the art will be familiar with the variety of detection systems that can be utilized in the methods of the invention.

The invention also relates in some aspects to kits for measuring α-amylase activity in a flour or stock sample. The kits of the invention may include a first container of detectably labeled starch substrate, a second container of an α-amylase standard and instructions for measuring the α-amylase activity in a flour or stock sample. Some kits of the invention may include a container containing a starch substrate, a second container containing an α-amylase standard, a third container containing a detectable label, instructions for labeling the starch substrate, and instructions for measuring the α-amylase activity in a flour or stock sample. The kits of the invention may also include additional components such as tubes, vials, containers, dip sticks, buffers, water, etc. The kits of the invention may also be provided in conjunction with supplementary equipment (e.g. measuring devices such as fluorometers), and may also include instructions for running the assays of the invention utilizing the supplementary equipment.

EXAMPLES

Introduction

Wheat or fungal α-amylase activity in flour samples is tested. The method may also be used to measure the activity of other types of microbial α-amylase, such as bacterial α-amylase activity.

Methods

Standard Starch Solution

Add 1.053 g waxy maize starch (or other starch) to 75 ml distilled water and autoclave 30 minutes and cool. Add 10 ml of 500 mM imidazole-HCl buffer (pH 6.5), β-glycerol phosphate buffer, or other equivalent buffer, which can give optimum buffering at pH 6.5. The mixture is diluted to 100 ml with distilled water.

Standard Assay (Modified from Fox, J. D, and Robyt, J. F. *Anal. Biochem*, 195:93–96, 1991). 1.9 ml starch solution is incubated 2 min at desired temperature. 100 μl amylase preparation (diluted as necessary with buffer) is added and incubated at ambient temperature. 100 μl samples are taken from the incubation mixture at 5, 10, 15, 20, and 30 min and added to Xμl of 0.01 M NaOH (X can range from 100 to 900 μl to give different dilutions). After all samples are taken, 100 μl of each sample is added to 100 μl of Cu-bicinchoninate working reagent in a microplate. The plate is incubated 35 min at 80° C., then is cooled and the absorbance is read. Maltose standards are prepared and 100 μl of each is added to 100 μl of Cu-bicinchoninate working reagent. The slope of the linear α-amylase curve (micromoles of maltose/min) is determined and used to calculate the number of units, using the maltose standard plot.

Preparation of a Fluorescent Starch Substrate for Use in Assaying α-Amylases

Starch, for example waxy maize starch, is activated by reaction with alkaline cyanogen bromide using the method of Cuatrecasas, P. and Anfinsen, C., *Meth. Enzymol.* 22:351–378, 1971. Activation is followed by reaction with a fluorescent dye that has a free amino group. The amino group of the fluorescent molecule reacts with the cyanogen-bromide-activated starch according to the following reactions, wherein R=ligand (e.g. fluorescent or enzyme).

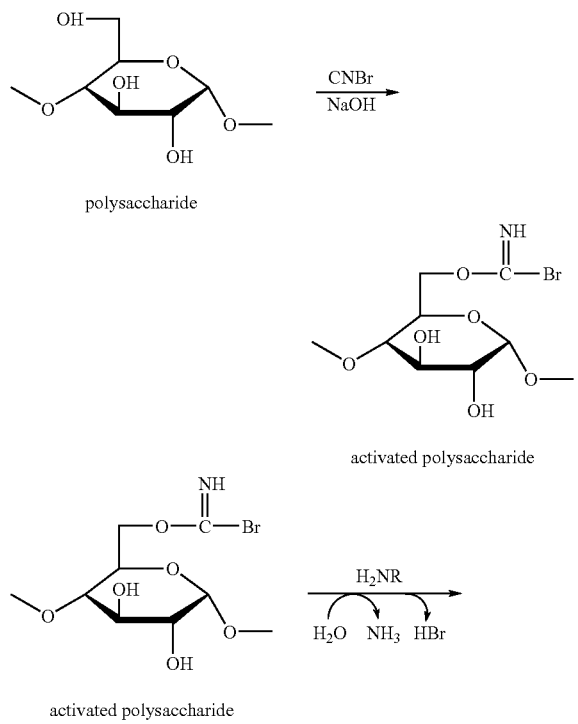

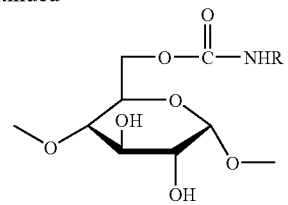

ligand or enzyme coupled to polysaccharide

The amount of derivatization of the starch is kept to 1 in 10 or 1 in 15 D-glucose residues to allow α-amylase to react with the derivatized starch. The labeling ratio can be determined by mass spectrometry and NMR using standard methods. It can also be determined by measuring the quantity of fluorescence labeling of D-glucose residues. The number of fluorescent molecules can be calculated by the absorbance coefficient, while the number of micromoles of glucose can be determined by the micro phenol-sulfuric acid method using standard procedures.

Assay for α-Amylase Activity (A)

Water is added to a flour sample to liquefy and make a slurry. A known amount of prepared liquefied flour is added to an aliquot of prepared substrate (fluorescent starch). The mixture is incubated at ambient temperature. The reaction mixture is added to a filtration device that will retain the starch and flour particles but permit hydrolyzed detectably labeled fragments to pass. The filtrate is mixed well and read in a calibrated fluorometer to determine amylase activity.

Assay for α-Amylase Activity (B)
1) 200 mg fluorescent starch is suspended in 1 ml buffer.
2) The 1-ml sample to be assayed is added to the starch.
3) The samples are mixed and reaction allowed to proceed.
4) The reaction mixture is then mixed again and centrifuged and aliquots are taken from the supernatant for measurement of the fluorescence. The level of fluorescence is proportional to the amount of α-amylase activity in the sample.
5) Alternatively, samples are continuously stirred and aliquots are taken as described in step 3, centrifuged, and fluorescence measured as in step 4.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety.

We claim:

1. A method for measuring α-amylase activity in a flour or stock sample, comprising
forming a reaction mixture by contacting a flour or stock sample with a detectably labeled starch substrate, for a time sufficient for α-amylase in the sample to hydrolyze the starch substrate, thereby releasing soluble detectably labeled starch fragments,
separating the soluble detectably labeled starch fragments from the reaction mixture, wherein separating comprises contacting the fragments with an agent that binds to the detectably labeled starch fragments, and determining the level of hydrolysis of the detectably labeled starch substrate as a measurement of α-amylase activity in the flour or stock sample.

2. The method of claim 1, wherein determining the level of hydrolysis of the detectably labeled starch substrate comprises quantifying the detectably labeled starch substrate.

3. The method of claim 1, further comprising calculating the α-amylase activity in the sample by correlating the quantity of detectably labeled starch to an α-amylase standard.

4. The method of claim 1, wherein the detectably labeled starch substrate is a waxy maize starch.

5. The method of claim 1, wherein the detectably labeled starch substrate comprises D-glucose residues and is labeled on about one of every 5–20 D-glucose residues of the starch substrate.

6. The method of claim 1, wherein the starch substrate is detectably labeled with a label compound selected from the group consisting of fluorescent, enzyme, radioactive, metallic, biotin, chemiluminescent, bioluminescent, and chromophore molecules.

7. The method of claim 1, wherein the step of separating the soluble detectably labeled starch fragments from the reaction mixture further comprises filtering the reaction mixture to remove from the mixture detectably labeled starch substrate.

8. The method of claim 1, wherein the agent is a lectin.

9. The method of claim 1, wherein the agent is an antibody.

10. The method of claim 1, wherein the sample is an aqueous slurry.

11. A method for measuring α-amylase activity in a flour or stock sample, comprising forming a reaction mixture by contacting a flour or stock sample with a detectably labeled starch substrate attached to a surface, for a time sufficient for α-amylase in the flour sample to hydrolyze the starch substrate, thereby releasing soluble detectably labeled starch fragments, separating the soluble detectably labeled starch fragments from the reaction mixture, wherein separating comprises contacting the fragments with an agent that binds to the detectably labeled starch fragments, and determining the level of hydrolysis of the detectably labeled starch substrate as a measurement of α-amylase activity in the flour or stock sample.

12. The method of claim 11, wherein the surface is selected from the group consisting of a tube, a centrifuge tube, a cuvette, a dipstick, a multiwell plate, a slide, a coverslip, a card, a bead, and a plate.

13. The method of claim 11, wherein determining the level of hydrolysis of the detectably labeled starch substrate comprises quantifying the soluble detectably labeled starch substrate fragments.

14. The method of claim 13, further comprising calculating the α-amylase activity in the sample by correlating the quantity of soluble detectably labeled starch fragments to an α-amylase standard.

15. The method of claim 11, wherein determining the level of hydrolysis of the detectably labeled starch substrate comprises quantifying the detectably labeled starch substrate after separating the soluble detectably labeled starch fragments from the reaction mixture.

16. The method of claim 11, further comprising, releasing the detectably labeled starch substrate from the surface after separating the soluble detectably labeled starch fragments from the reaction mixture.

17. The method of claim 16, wherein determining the level of hydrolysis of the detectably labeled starch substrate comprises quantifying the detectably labeled starch substrate after releasing the detectably labeled starch substrate from the surface.

18. The method of claim 11, further comprising calculating the α-amylase activity in the sample by correlating the quantity of detectably labeled starch to an α-amylase standard.

19. The method of claim 11, wherein the detectably labeled starch substrate is a waxy maize starch.

20. The method of claim 11, wherein the detectably labeled starch substrate comprises D-glucose residues and is labeled on about one of every 5–20 D-glucose residues of the starch substrate.

21. The method of claim 11, wherein the starch substrate is detectably labeled with a label compound selected from the group consisting of fluorescent, enzyme, radioactive, metallic, biotin, chemiluminescent, bioluminescent, and chromophore molecules.

22. The method of claim 11, wherein the step of separating the soluble detectably labeled starch fragments from the reaction mixture further comprises filtering the reaction mixture to remove from the mixture detectably labeled starch substrate.

23. The method of claim 11, wherein the agent is a lectin.

24. The method of claim 11, wherein the agent is an antibody.

25. The method of claim 11, wherein the sample is an aqueous slurry.

* * * * *